United States Patent
Zenk et al.

(10) Patent No.: US 7,553,829 B2
(45) Date of Patent: Jun. 30, 2009

(54) TREATMENT OF CHRONIC FATIGUE SYNDROME AND FIBROMYALGIA SYNDROME

(75) Inventors: Ronald J. Zenk, Shorewood, MN (US); John L. Zenk, Minnitrista, MN (US)

(73) Assignee: Humanetics Corporation, Eden Prairie, MN (US)

( * ) Notice: Subject to any disclaimer, the term of this patent is extended or adjusted under 35 U.S.C. 154(b) by 1161 days.

(21) Appl. No.: 10/433,043

(22) PCT Filed: Oct. 31, 2001

(86) PCT No.: PCT/US01/46241

§ 371 (c)(1), (2), (4) Date: May 27, 2003

(87) PCT Pub. No.: WO02/43737

PCT Pub. Date: Jun. 6, 2002

(65) Prior Publication Data

US 2004/0038955 A1 Feb. 26, 2004

Related U.S. Application Data

(60) Provisional application No. 60/250,227, filed on Nov. 30, 2000.

(51) Int. Cl.
*A61K 31/56* (2006.01)
(52) U.S. Cl. .................. 514/181; 514/171; 514/182
(58) Field of Classification Search ............... 514/181, 514/171, 182
See application file for complete search history.

(56) References Cited

U.S. PATENT DOCUMENTS

| | | | |
|---|---|---|---|
| 5,206,008 A | 4/1993 | Loria | |
| 5,292,730 A | 3/1994 | Lardy | |
| 5,296,481 A | 3/1994 | Partridge et al. | |
| 5,461,042 A | 10/1995 | Loria | |
| 5,585,371 A | 12/1996 | Lardy | |
| 5,641,766 A | 6/1997 | Lardy | |
| 5,641,768 A | 6/1997 | Loria | |
| 5,707,983 A | 1/1998 | Lardy | |
| 5,885,977 A | 3/1999 | Pauza et al. | |
| 5,900,420 A | 5/1999 | Cole | |
| 5,919,460 A | 7/1999 | Ingram | |
| 5,935,949 A * | 8/1999 | White | 514/178 |
| 5,990,162 A | 11/1999 | Scharf | |
| 6,372,732 B1 | 4/2002 | Lardy et al. | |
| 6,489,313 B1 | 12/2002 | Lardy et al. | |

FOREIGN PATENT DOCUMENTS

| | | | |
|---|---|---|---|
| DE | 873699 | | 4/1953 |
| JP | 45-37770 | | 3/1966 |
| WO | WO99/25192 | * | 5/1999 |

OTHER PUBLICATIONS

Lahita RG., Collagen disease: the enemy within. Int. J. Fertile Women's Med. Sep.-Oct 1998; 43(5):229-34.
Kizildere S., During a corticotropin-releasing hormone test in healthy subjects administration of a beta-adrenergic antagonist induced secretion of cortisol and dehydroepiandrosterone sulfate and inhibited secretion of ACTH, Eur. J Endocrinol. 2003;148(1):45-53.
Scott LV., Differences in adrenal steroid profile in chronic fatigue syndrome, in depression and in health. Journal of Affective Disorders, 1999 ; 54(1-2):129-37.
De Becker P. Dehydroepiandrosterone (DHEA) Response to i.v. SCTH in Patients with Chronic Fatigue Syndrom, Horm Metab Res 1999; 31:18-21.
Kuratsune H., Dehydroepiandrosterone sulfate deficiency in chronic fatigue syndrome, International Journal of Molecular Medicine, 1998:143-146.
Nelson R., Dehydroepiandrosterone and 7-Keto DHEA Augment Interleukin 2(IL-2) Production by Human Lymphocytes in Vitro, Feb. 1998 Chicago, IL.

* cited by examiner

*Primary Examiner*—San-ming Hui
(74) *Attorney, Agent, or Firm*—Sherrill Law Offices, PLLC

(57) ABSTRACT

Chronic fatigue syndrome (CFS) and fibromyalgia syndrome (FMS) can be treated by the administration of Δ5-androstene-3β-ol-7,17 dione and metabolizable precursors thereof.

7 Claims, No Drawings

TREATMENT OF CHRONIC FATIGUE SYNDROME AND FIBROMYALGIA SYNDROME

This application is the U.S. National Stage Application of International Application No. PCT/US01/46241, filed Apr. 21, 2000, which claims the benefit of U.S. Provisional Application No. 60/250,227, filed Nov. 30, 2000.

FIELD OF THE INVENTION

This invention broadly relates to the treatment of chronic fatigue syndrome (CFS) and fibromyalgia syndrome (FMS). More specifically, the invention relates to prophylactic, modulatory, ameliorative and curative drug therapies for CFS and FMS.

BACKGROUND

Chronic fatigue syndrome (CFS) is a clinically defined condition characterized by severe disabling flu-like fatigue and a combination of symptoms that include impairment in concentration and short-term memory, sleep disturbances, and musculosketetal pain.

Fibromyalgia syndrome (FMS) is a chronic rheumatic condition characterized by systemic body pain and uncontrollable fatigue. Many other symptoms are associated with FMS, such as headaches, sleep disorders and poor circulation.

CFS and FMS remain serious problems for a large segment of the general population. While many medications are commonly used to treat these conditions, there are no known medications which permanently resolve the symptoms of either CFS or FMS and many of the currently used medications produce undesirable side effects ranging from drowsiness and dizziness to addiction and liver damage.

Some of the more common medications employed to treat CFS and/or FMS include analgesics, hypnotics, immune suppressants and an array of herbal and dietary supplements.

Analgesics include nonsteroidal anti-inflammatory drugs. An analgesic that is sometimes prescribed for CFS and FMS patients is cyclobenzaprine. It is generally prescribed for the relief of skeletal muscle spasms.

Hypnotics used in the treatment of CFS and FMS include the benzodiazepines. Benzodiazepines are typically prescribed for CFS patients as a treatment for various sleep disorders. Examples of benzodiazepines used in the treatment of CFS and FMS are Klonopin™, Valium™, Xanax™, Ativan™, and Dalmane™. A non-benzadiazepine hypnotic drug that has sometimes been prescribed to relieve sleep problems for CFS patients if Zolpidem™.

Immune suppressants prescribed to treat CFS and FMS include azathioprine. Such use is purely experimental and generally considered inappropriate for the treatment of CFS and FMS in view of the degree of toxicity associated with these agents.

Other drugs given to treat CFS and FMS include Naltrexoned™, opioid antagonist, sodium retention agents, beta blockers, calcium channel blockers, histamine blockers, antidepressants, allergy medications, and acute anxiety medications. Most of these drugs are either inappropriate for the treatment of CFS and FMS either because they are not effective or because of the significant side effects associated with their use.

A wide variety of herbal preparations, and dietary supplements have been suggested for use in alleviating the symptoms of CFS and/or FMS. One such herbal preparation is disclosed in U.S. Pat. No. 5,919,460. Although the potential medicinal value of various herbs is promising, it is difficult, if not impossible, to assess the validity of scientific claims regarding these substances.

Other medications recently suggested for the treatment of CFS and/or FMS include buprenorphine (U.S. Pat. No. 5,900, 420) and various esters and salts of 4-hydroxybutyric acid (U.S. Pat. No. 5,990,162).

U.S. Pat. No. 5,935,949 discloses that the symptoms of CFS and FMS can be alleviated through androgen therapy. However, the prolonged administration of adrogens involves a number of undesirable side effects such as hirsutism in women.

While a number of options exist for the treatment of CFS and/or FMS, a need continues to exist for a composition that is effective in treating CFS and/or FMS in the absence of any significant undesirable side effects.

SUMMARY OF THE INVENTION

The invention is directed to the administration of Δ5-androstene-3β-ol-7,17 dione and And metabolizable precursors thereof for the prophylactic, modulatory, ameliorative and curative treatment of chronic fatigue syndrome (CFS) and fibromyalgia syndrome (FMS).

DETAILED DESCRIPTION OF THE INVENTION INCLUDING A BEST MODE

Chronic fatigue syndrome and fibromyalgia syndrome can be treated by administering therapeutic amounts of the steroid Δ5-androstene-3β-ol-7,17 dione and metabolizable precursors thereof such as Δ5-androstene-3β-acetyl-7,17 dione. Such treatment can be prophylactic, modulatory, ameliorative or curative in nature.

The Compound

The steroid Δ5-androstene-3β-ol-7,17 dione is a derivative of dehydroepiandrosterone (DHEA) which does not appreciably stimulate, increase or otherwise enhance the production of sex hormones. The steroid is commercially available from a number of sources including Steraloids, Inc. of Wilton, N.H. A number of procedures are available for synthesizing Δ5-androstene-3β-ol-7,17 dione from DHEA, with one such procedure described in U.S. Pat. No. 5,296,481.

Precursors of Δ5-androstene-3β-ol-7,17 dione may also be usefully employed in the treatment of hypothyroidism. Such precursors are readily metabolized in vivo to the active Δ5-androstene-3β-ol-7,17 dione. One example of such a metabolizable precursor is the commercially available Δ5-androstene-3β-acetyl-7,17 dione. The 3β-acetyl group is hydrolyzed in vivo by esterases located in the blood and various tissue to produce the active Δ5-androstene-3β-ol-7, 17 dione, and is believed to be less susceptible to oxidation during the manufacturing process than the hydroxy group found on the active Δ5-androstene-3β-ol-7,17 dione. Other metabolizable precursors include Δ5-androstene-3β, 17(3-diol-7-one, Δ5-androstene-3β, 7α-diol-17-one, Δ5-androstene-3β, 7β-diol-17-one and the corresponding acetyl esters of these steroids.

Administration

Administration Route

The Δ5 Androstene-3-acetyl-7,17-dione can be administered by virtually any of the commonly accepted practices for the administration of pharmaceutical preparations including specifically, but not exclusively, mucosal administration, oral consumption, ocular administration, subcutaneous injection, transdermal administration, etc. Oral administration is generally preferred.

Mucosal administration of the steroid includes such routes as buccal, endotracheal, nasal, pharyngeal, rectal, sublingual, vaginal, etc. For administration through the buccal/sublingual/pharyngeal/endotracheal mucosal, the steroid may be formulated as an emulsion, gum, lozenge, spray, tablet or an inclusion complex such as cyclodextrin inclusion complexes. Nasal administration is conveniently conducted through the use of a sniffing powder or nasal spray. For rectal and vaginal administration the steroid may be formulated as a cream, douche, enema or suppository.

Oral consumption of the steroid may be effected by incorporating the steroid into a food or drink, or formulating the steroid into a chewable or swallowable tablet or capsule.

Ocular administration may be effected by incorporating the steroid into a solution or suspension adapted for ocular application such as drops or sprays.

Subcutaneous administration involves incorporating the steroid into a pharmaceutically acceptable and injectable carrier.

For transdermal administration, the steroid may be conveniently incorporated into a lipophilic carrier and formulated as a topical creme or adhesive patch.

Dose Rate

The range of dosages and dose rates effective for achieving the desired biological response may be determined in accordance with standard industry practices. These ranges can be expected to differ depending upon numerous well known factors such as the severity and/or chronicity of the disease, the species of the patient, the histopathalogic type of the patient, the weight of the patient, the length and course of the treatment, the responsiveness of the patient, and whether the desired response is prophylactic, modulatory, ameliorative or curative in nature.

The treatment of CFS and FMS is often idiosyncratic and adjustment of dosages and dose rate is well within the level of one having skill in the art.

Subject

The subject can be a human or a pet such as a cat, dog or horse. The treatment is also suitable for use with commercially valuable livestock such as cattle, pigs and sheep; as well as exotic mammals such as those found in zoos and circuses.

EXPERIMENTAL

Experiment 1

One male subject, aged 73, recently diagnosed with chronic fatigue syndrome by CDC criteria, orally consumed 100 mg capsules of Δ5-androstene-3-acetyl-7,17-dione twice daily for two months. Upon a visit to his personal physician, he reported an 80% improvement in his symptoms of fatigue and felt more mentally alert. As testament to his improvement, he reported to his physician that he had just finished building a 20'×30' addition to his barn, something, he said, he would not have and could not have done prior to taking Δ5-androstene-3-acetyl-7,17-dione.

We claim:

1. A method of treating chronic fatigue syndrome comprising administering a therapeutically effective amount of a compound to a mammal in need of such treatment wherein the compound is selected from Δ5-androstene-3β-ol-7,17 dione, Δ5-androstene-3β, 17β-diol-7-one, Δ5-androstene-3β, 7α-diol-17-one, Δ5-androstene-3β, 7β-diol-17-one and the corresponding acetyl esters of these steroids.

2. The method of claim 1 wherein the subject is a mammal.

3. The method of claim 2 wherein the subject is a dog or a cat.

4. The method of claim 2 wherein the subject is a human.

5. The method of claim 1 wherein the compound is administered orally.

6. The method of claim 1 wherein the compound is Δ5-androstene-3β-acetoxy-7,17 dione.

7. The method of claim 1 wherein the compound is administered daily.

* * * * *